United States Patent [19]

Riscoe et al.

[11] Patent Number: 4,820,692
[45] Date of Patent: Apr. 11, 1989

[54] METHYLTHIORIBOSE ANALOGS, THEIR PREPARATION AND USE AS MEDICINAL AGENTS AND BIOCIDES

[75] Inventors: Michael K. Riscoe, Tualatin; John H. Fitchen, Portland; Adolph J. Ferro, Corvallis, all of Oreg.

[73] Assignee: State of Oregon, acting by and through the Oregon State Board of Higher Education, acting for and on behalf of the Oregon Health Sciences University and Oregon State University, Portland, Oreg.

[21] Appl. No.: 1,778

[22] Filed: Jan. 9, 1987

Related U.S. Application Data

[63] Continuation-in-part of Ser. No. 823,929, Jan. 30, 1986, abandoned.

[51] Int. Cl.$^4$ .................. A61K 31/70; C07H 15/00; C07H 15/04; C12P 13/12
[52] U.S. Cl. .................................. 514/23; 536/18.4; 536/120; 536/122; 536/1.1; 435/113
[58] Field of Search .............. 536/18.4, 120, 122, 536/1.1, ; 514/706, 23; 435/113

[56] References Cited

U.S. PATENT DOCUMENTS 3,817,978 6/1974 Jenkins et al. .................. 536/18.4

FOREIGN PATENT DOCUMENTS 39-17266 8/1964 Japan .................. 536/124

OTHER PUBLICATIONS

Pigman; (Ed.) *The Carbohydrates* pp. 554, 555 and 558, (1957) Academic Press Inc.
Matsuura, A. et al: Chemical Abstracts, vol. 103 (1985) 64402k.
Cech, D. et al: Chemical Abstracts, vol. 96 (1982) 143238b.
Wang, Y. et al: Carbohydrate Research 76:131-140 (1979).

Primary Examiner—Ronald W. Griffin
Assistant Examiner—Nancy S. Carson
Attorney, Agent, or Firm—Millen & White

[57] ABSTRACT

Compounds of the formula:

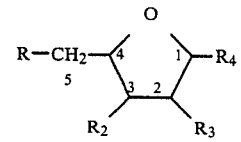

wherein R is H, Cl, F, Br, I or $R_1S-$, in which $R_1$ is $C_1-C_{10}$ linear or branched chain alkyl or halogenated linear or branched chain alkyl, and
wherein $R_2$, $R_3$ and $R_4$ are the same or different and each is H— or —OH,
with the proviso that at least one of $R_2$, $R_3$ and $R_4$ is hydroxy and the further proviso that when $R_2$, $R_3$ and $R_4$ are all OH, $R_1$ is other than methyl, are useful in inhibiting the growth of MTR kinase-dependent microorganisms and parasitic protazoans. The compounds wherein R is $R_1S$ are novel, except those wherein $R_1$ is methyl or isobutyl when $R_2$, $R_3$ and $R_4$ are all OH.

53 Claims, No Drawings

METHYLTHIORIBOSE ANALOGS, THEIR PREPARATION AND USE AS MEDICINAL AGENTS AND BIOCIDES

This invention was made with government support under contract DHHS National Cancer Institute #5-K04-CA00617-05. The government has certain rights in this invention.

RELATED APPLICATIONS

This application is a continuation in part of application Ser. No. 823,929 filed Jan. 30, 1986, now abandoned.

BACKGROUND OF THE INVENTION

The present invention relates to novel methylthioribose analogues and their use as medicinal and biocidal agents.

5-Deoxy-5-methylthioribose (MTR) is a naturally occurring compound derived from 5′-deoxy-5′-methylthioadenosine (MTA). MTR is essential in the salvage of methionine in organisms containing the enzyme MTR kinase. MTR is a substrate for MTR kinase, and its carbohydrate and alkylthio moeities are recycled into methionine. Methionine, an essential amino acid, is required for DNA/RNA/protein synthesis.

U.S. Pat. No. 4,420,489 discloses 5-thio-D-ribose and 5-thio-2-deoxyribose (compounds in which the ring oxygen atom is replaced by a sulfur atom) as agents capable of preventing radiation damage.

U.S. Pat. Nos. 3,836,644; 3,767,800 and 4,481,196 disclose glycoside phosphate derivatives, some of which could be regarded in the broadest sense as analogs of MTR. In each case, the compounds demonstrate some physiological activity, but not biocidal activity.

U.S. Pat. No. 4,378,369 discloses that some mono- and diesters of 2,5-anhydro-D-mannitol are useful in treating diabetes. These compounds are similar, but not identical to MTR.

U.S. Pat. No. 4,243,663 discloses an adjuvant compound based on fructose instead of ribose.

U.S. Pat. No. 4,086,076 discloses tetrahydrofuranyl based compounds with fungicide and bacteriacide properties.

U.S. Pat. No. 2,840,587 discloses the synthesis of ethionine.

U.S. Pat. No. 4,080,465 discloses cyclic thio compounds.

Shapiro et al., Biochem. Biophys. Res. Comm., 102:302 (1981), discloses that MTR is the precursor of methionine in procaryotic microorganisms.

Schroeder et al., Can. J. Microbiol., 19, 1347 (1973), discloses the production of MTR in *E. coli*. The article further indicates that MTA is the precursor of MTR in procaryotic microorganisms.

Kikugawa et al., Tetrahedron Letters 2, 87–90 (1971), describes the synthesis of 5′-chloro-5′-deoxy-adenosine and similar compounds which serve as synthetic starting points for ethylthioadenosine (ETA). Biochem. Biophys. Acta., 320 357–362 (1973), describes the preparation of MTR.

Plant Physiology 71; 932 (1983) and Eur. J. Biochem. 87; 257 (1978) disclose isobutylthioribose.

Eur. Biochem., 87, 257 (1978) discloses 5-S-(2-methylpropyl)-5-thio-D-ribose.

Chem. Lett. 819 (1979) discloses orthophenylmethyl thioribose.

Agents for systemically treating fungal infections are known. Amphoterecin-B is frequently prescribed; however, it can cause undesirable side effects, e.g., renal failure.

OBJECTS OF THE INVENTION

It is an object of this invention to provide novel methylthioribose analogs which have improved properties, e.g., those discussed below.

It is a further object of this invention to provide a method of treating mammals infected with a microorganism with a methylthioribose analogue.

Yet another object of this invention is to provide a method of inhibiting the growth of infectious microorganisms with a methylthioribose analogue.

Upon further study of the specification and appended claims, further objects and advantages of this invention will become apparent to those skilled in the art.

SUMMARY OF THE INVENTION

In a composition aspect, this invention relates to compounds of Formula I

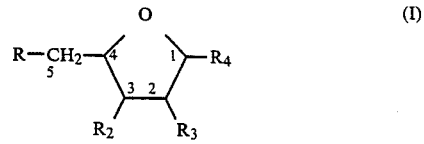

wherein R is H, Cl, F, Br, I or $R_1S$— in which $R_1$ is $C_1$–$C_{10}$ linear or branched chain alkyl or halogenated $C_1$–$C_{10}$ linear or branched chain alkyl,
wherein
$R_2$, $R_3$ and $R_4$ are the same or different and each is H or —OH,
with the proviso that at least one of $R_2$, $R_3$ and $R_4$ is hydroxy and the further proviso that when $R_2$, $R_3$ and $R_4$ are all OH, $R_1$ is other than methyl or isobutyl.

In another composition aspect, this invention relates to a pharmaceutical composition in unit dosage form comprising, in admixture with a pharmaceutically acceptable carrier an amount per unit dosage effective to inhibit the growth of *Candida albicans* of a compound of Formula I
wherein R is H, Cl, F, Br, I or $R_1S$— in which $R_1$ is $C_1$–$C_{10}$ linear or branched chain alkyl or halogenated $C_1$–$C_{10}$ linear or branched chain alkyl,
wherein
$R_2$, $R_3$ and $R_4$ are the same or different and each in H or —OH,
with the proviso that at least one of $R_2$, $R_3$ and $R_4$ is H— or —OH and the further proviso that when $R_2$, $R_3$ and $R_4$ are all —OH, $R_1$ is other than methyl.

In a method aspect, this invention relates to a method of treating a mammal infected with a microorganism, comprising administering systemically thereto an amount effective to ameliorate the infection, of a compound of the Formula I
wherein R is H, Cl, F, Br, I or $R_1S$— in which $R_1$ is $C_1$–$C_{10}$ linear or branched chain alkyl or halogenated $C_1$–$C_{10}$ linear or branched chain alkyl,
wherein
$R_2$, $R_3$ and $R_4$ are the same or different and each is H or —OH,
with the proviso that at least one of $R_2$, $R_3$ and $R_4$ is hydroxy and the further proviso that when $R_2$, $R_3$ and $R_4$ are all —OH, $R_1$ is other than methyl.

In another method aspect, this invention relates to a method of inhibiting the growth of an MTR kinase-containing microorganism, comprising applying to the habitat thereof a metabolization-inhibiting amount of a compound of Formula I
wherein R is H, Cl, F, Br, I or $R_1S$— in which $R_1$ is $C_1$-$C_{10}$ linear or branched chain alkyl or halogenated $C_1$-$C_{10}$ linear or branched chain alkyl,
wherein
$R_2$, $R_3$ and $R_4$ are the same or different and each is H or —OH,
with the proviso that at least one of $R_2$, $R_3$ and $R_4$ is hydroxy and the further proviso that when $R_2$, $R_3$ and $R_4$ are all OH, R, is other than methyl.

In another method aspect, this invention relates to a method of treating a mammal infected with a protozoan comprising administering thereto an amount effective to ameliorate the infection, of a compound of Formula I,
wherein R is H, Cl, F, Br, I or $R_1S$— in which $R_1$ is $C_1$-$C_{10}$ linear or branched chain alkyl or halogenated linear or branched chain alkyl,
wherein
$R_2$, $R_3$ and $R_4$ are the same or different and each is H or —OH,
with the proviso that at least one of $R_2$, $R_3$ and $R_4$ is —OH and the further proviso that when $R_2$, $R_3$ and $R_4$ are all —OH, $R_1$ is other than methyl.

DETAILED DISCUSSION

This invention is based on the discovery that analogues of MTR inhibit the growth of a wide variety of pathogenic microorganisms. A class of microorganisms inhibited by MTR analogues are MTR kinase-containing microorganisms. MTR kinase is present in many microorganisms, e.g., fungi, bacteria and some types of plants, e.g., tomatoes, apples and avocados.

MTR is synthesized from MTA (5'-Deoxy-5'-methylthioadenosine) via MTA nucleosidase and is a substrate for MTR kinase. Neither of these enzymes is found in mammal cells. The product of the kinase activity, MTR-1-phosphate, is recycled into methionine, which is essential for DNA/RNA and protein synthesis.

It is believed that some of the compounds of this invention manifest their activity by inhibiting the production of methionine and that other compounds of the invention may also function as a substrate for MTR kinase and produce toxic metabolic analogs of methionine, and other analogues possibly function to inhibit growth in a manner distinct from MTR kinase and the methionine recycling pathway. For example, ethionine is known to be toxic (see "Molecular Aspects of the In Vivo and In Vitro Effects of Ethionine, an Analog of Methionine," microbiological Reviews, Vol. 46, 283-295). Trifluoromethionine is also toxic.

Examples of $R_1$ alkyl groups are ethyl, propyl, isopropyl, butyl, isobutyl, tertbutyl, pentyl, neopentyl, hexyl, heptyl, decyl, etc. The $R_1$ alkyl groups can optionally be mono- to poly-substituted by halogen atoms, e.g., $R_1$ can be chloromethyl, chloroethyl, dichloromethyl, 1,1-dichloroethyl, 1,2-dichloroethyl, bromomethyl, iodomethyl, etc.

Compounds of Formula I where R is $R_1S$ in which $R_1$ is $C_1$-$C_{10}$ linear or branched chain alkyl or halogenated $C_1$-$C_{10}$ linear or branched chain alkyl, wherein $R_2$, $R_3$ and $R_4$ are the same or different and each is H— or —OH with the proviso that at least one of $R_2$, $R_3$ and $R_4$ is hydroxy and when $R_2$, $R_3$ and $R_4$ are all OH, $R_1$ is other than methyl, or isobutyl (which latter compounds are known in the prior art).

The compounds of Formula I can be prepared by conventionally reacting a conventional compound of Formula II

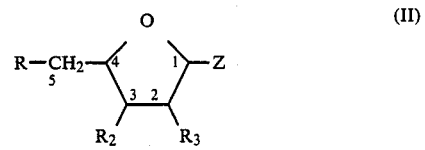

wherein $R_2$ and $R_3$ are the same or different and each is H or —OH and Z is hydrolyzable by cleavage in acid solution, (e.g., Z is adenine, guanine, cytosine, uracil, thymine, etc.). The 5' position of the nucleoside is susceptible to suitable halogenating agents, e.g., thionyl chloride or thionyl bromide. The resultant 5'-halogenatednucleoside can be directly hydrolyzed to the corresponding 5-halogenated compounds of Formula I. Alternatively, the 5'-halogenated nucleoside of Formula II can be converted to the corresponding 5'-alkylthiol derivative by reaction with an alkylthiol, e.g., methylthiol, ethylthiol, etc., in liquid $NH_3$ in the presence of sodium metal. In general, the reaction is carried out under conditions wherein one ml of liquid $NH_3$ is employed for each mmole of nucleoside to be added and, in general, a 3-fold excess of alkyl mercaptan is employed. In general, the reaction proceeds for 1-2 hours. The aqueous fraction is preferably concentrated in vacuo from which the resultant crystals may be collected. Preferably, the resultant crystals are purified by thin layer chromatography. The purified alkylthiol-nucleosides are then hydrolyzed to the appropriate alkylthiol-containing compound by simple acid-catalyzed hydrolysis, e.g., by suspending the nucleoside in a solution of HCl at 100° C. After the reaction has progressed substantially to completion the reaction mixture is cooled and the pH is raised, e.g., to 3.5. The desired product can be separated from the other hydrolysis products, e.g., adenine and any residual unhydrolyzed nucleoside, by cation exchange chromatography.

In general, the preparation of the compounds of Formula I is fully conventional and employs conditions well known to those in the art, perhaps requiring only a few routine orientation experiments to determine optimal parameters. The compounds of Formula II are all well known or can be conventionally prepared from known starting materials. The preparation of compounds of Formula I may proceed with or without racemization.

The compounds of Formula I are valuable biocides and useful as pharmaceuticals. In general, the compounds of Formula I have no apparent effect on the growth and differentiation of non-MTR kinase-dependent microorganisms. Thus, the compounds can be used in the treatment of mammals infected with an MTR kinase-dependent microorganism to ameliorate the infection without adversely affecting the infected host. Additionally, the compounds of Formula I can be employed to kill or inhibit the growth of MTR kinase-dependent microorganisms by applying them to the habitat of such microorganisms. Often such a habitat is mammalian skin. Thus, compounds of Formula I are also suitable for topical application. The compounds of Formula I are acid-stable and stable at elevated temperatures. Thus, they are especially suitable for oral administration.

In general, the compounds of Formula I are effective to inhibit the growth of any MTR kinase-containing microorganism.

The following fungi are illustrative of those whose growth is inhibited by the MTR analogues of this invention: *Candida albicans, Cryptococcus neoformans, Blastomyces dermatitidis, Histoplasma casulatum, Coccidioides immitis, Para coccidioides brasiliensis.*

Examples of bacteria whose growth is inhibited by the MTR analogues of this invention are: *Enterobacter aerogenes, Staphylococcus aures.*

The above lists are not all-inclusive.

MTR kinase-containing microorganisms can be identified by the following method: the assay mixture contains 50 mMolar imidazole-HCl (pH 7.3), 0.1 mMolar [methyl-$C^{14}$] methylthioribose ($5 \times 10^6$ CPM/$\mu$M0, 1.0 mMolar ATP, 5.0 mMolar $MgSO_4$, 10 mMolar dithiothreitol and cell extract in a total volume of 0.2 ml. After incubation at 37° C. for 20 minutes, the reaction is stopped by addition of 3 volumes of ice-cold ethanol and the precipitated protein is removed by centrifugation. A 0.2 ml aliquot of the supernatant fluid is then applied to a DOWEX-1-X8 formate column ($0.7 \times 2$ cm) and washed with 0.01N sodium formate. The product of the reaction, [methyl-$C^{14}$]-MTR-1-phosphate, is eluted with 12 ml 0.75N sodium formate. 3 ml of the eluant is combined with scintillation fluid and the amount of product formed is determined by scintillation counting. A reading above background indicates a positive test.

Formula I is not all-inclusive of compounds effective to inhibit the growth of MTR kinase-containing microorganisms. Thus, any compound which is a substrate for MTR kinase or competes with binding of MTR kinase to MTR can be employed to inhibit the growth of MTR kinase-containing microorganisms or to treat a mammal infected with an MTR kinase-containing microorganism to ameliorate the infection. The use of such compounds is a contemplated equivalent of this invention.

In general, compounds of this invention can be used to treat any infection of a mammal with an MTR kinase-containing microorganism. Specific examples of diseases which can be treated include: Candidiasis; skin lesions, systemic bacteremia, e.g., oral Candidiasis (thrush), Vulvovaginal Candidiasis, Intertridinous Candidiasis, Branchopulmonary Candidiasis, Cryptococcal meningitis, North American blastomycosis, Histoplasmosis, Coccidioidomycosis, Paracoccidioidomycosis.

The compounds of this invention can be employed to treat, mammals, e.g., humans, infected with protozoans, e.g., parasitic protozoans, e.g., *Plasmodium falciparum* (responsible for malaria), *Giardia lamblia* (responsible for "hiker's sickness") and *Ochromonas malhamensis.*

The pharmacologically active compounds of this invention can be processed in accordance with conventional methods of galenic pharmacy to produce products for administration to patients, e.g., mammals including humans. Conventional excipients are pharmaceutically acceptable organic or inorganic carrier substances suitable for parenteral or enteral or topical application which do not deleteriously react with the active compounds. Suitable pharmaceutically acceptable carriers include but are not limited to water, salt solutions, alcohols, gum arabic, vegetable oils, polyethylene glycols, gelatin, lactose, amylose, magnesium stearate, talc, silicic acid, viscous paraffin, perfume oil, fatty acid monoglycerides and diglycerides, pentaerythritol fatty acid esters, hydroxymethylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are injectable sterile solutions, preferably oil or aqueous solutions, as well as suspensions, emulsions, or implants, including suppositories. Ampoules are convenient unit dosages.

For enteral administration, particularly suitable are tablets, dragees, suppositories or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated, including those wherein the active compound is protected with differentially degradable coatings, e.g., by microencapsulation, multi coatings, etc.

Generally the compounds of this invention are dispensed in unit dosage form comprising 150–1,500 mg in a pharmaceutically acceptable carrier unit dosage.

The dosage of the compounds according to this invention generally is 5–30 mg/kg/day when adminstered to patients, e.g., humans, as an anti-fungal or anti-bacterial agent. Amphotericin-B is the currently prescribed known anti-fungal agent and the compounds of this invention can be administered similarly thereto.

Dosages for a given host can be determined using conventional considerations, e.g., by customary comparison of the differential activities of the subject compound and of a known agent, e.g., by means of an appropriate, conventional pharmacological protocol.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the preceding text and the following examples, all temperatures are set forth uncorrected in degrees Celsius and all parts and percentages are by weight, unless otherwise indicated.

EXAMPLE 1

5'-chloro-5'-deoxyadenosine

A solution of 0.75 ml of thionyl chloride and hexamethylphosphoramide is stirred under nitrogen while 0.5 gms of the nucleoside is added. The mixture is allowed to stir for 15–20 hours at room temperature, in ca. 20 mls of water. The pH is then neutralized to 7–8 with 2N $NH_4OH$. After cooling, the crystals are collected by filtration. The crystals are then applied to DOWEX-50H+, the resin washed well with water and then with 2N $NH_4OH$ to remove the product. After concentration, the second crop of crystals is collected by filtration. The crystals are 5'-chloro-5'-deoxyadenosine.

EXAMPLE 2

5'-chloro-2',5-deoxyadenosine

Analogously to Example 1, 2'-deoxyadenosine is converted to the captioned product.

EXAMPLE 3

5'-chloro-3',5'-deoxyadenosine

Analogously to Example 1, 3'-deoxyadenosine is converted to the captioned product.

EXAMPLE 4

5'-chloro-2',3'-deoxyadenosine

Analogously to Example 1, 2',3'-deoxyadenosine is converted to the captioned product.

EXAMPLE 5

5'-chloro-5'-deoxy-arabinoadenosine

Analogously to Example 1, arabinoadenosine is converted to the captioned product.

EXAMPLE 6

5'bromo-5'-deoxynucleosides

Analogously to Examples 1–5, the corresponding nucleosides therein are converted to the corresponding 5'-bromo-5'-deoxynucleosides by substitution of thionyl bromide for the thionyl chloride employed therein.

PREPARATION OF HALOGENATED DEOXYRIBOSES

EXAMPLE 7

5-deoxy-5-chlororibose (5-chlororibose)

The 5'-chloro-5'deoxy-adenosine of Example 1 is hydrolyzed to 5-chlororibose as follows: 20 mg of the nucleoside is suspended in 4 ml of 0.1M/HCl at 100° C. After 2.5–3 hours, the reaction mixture is cooled and the pH is raised to 3.5. Separation of 5-Chlororibose from adenine (the other hydrolysis product) and any residual unhydrolyzed nucleoside is accomplished through cation exchange chromatography using DOWEX-50H+. The measurement of the sugar concentration is determined using ribose as a standard in the phloroglucinol procedure detailed in Ashwell, G., (1972) Methods Enzymol 8, 85–95.

EXAMPLE 8

5-chloro-2,5-deoxyribose

Analogously to Example 7, the product of Example 2 is converted to the captioned product.

EXAMPLE 9

5-chloro-3,5-deoxyribose

Analogously to Example 7, the product of Example 3 is converted to the captioned product.

EXAMPLE 10

5-chloro-2,3-deoxyribose

Analogously to Example 7, the product of Example 4 is converted to the captioned product.

EXAMPLE 11

5-chloro-arabinose

Analogously to Example 7, the product of Example 5 is converted to the captioned product.

EXAMPLE 12

The corresponding 5-bromoriboses are prepared from the products of Example 6 analogously to the procedure in Example 7.

PREPARATION OF 5'-ALKYLTHIO-5'-DEOXYNUCLEOSIDES

The halogenated nucleosides of Examples 1–6 can be converted into the corresponding alkylthiodeoxynucleosides by reacting the products of Examples 1–6 with the appropriate alkylthiol, i.e., alkylmercaptan, to produce the desired alkylthiodeoxynucleoside. Accordingly, the following examples are merely illustrative.

EXAMPLE 13

5'-deoxy-5'-ethylthioadenosine

Liquid $NH_3$ is collected in a heavy glass tube immersed in a dry ice-ethanol bath. 1 ml of $NH_3$ is employed for each mole of 5'-chloro-5'-deoxyadenosine. A three-fold excess of ethanolthiol and a small amount of sodium methal is added. Dry 5'-chloro-5'-deoxyadenosine is added and the reaction proceeds for 1–2 hours. After the reaction is complete, the $NH_3$ is evaporated under vacuum and the residual mercaptan is removed by three successive ether extractions. The aqueous fraction is subsequently concentrated in vacuo, the resultant crystals are collected and the nucleoside purified by a thin layer of chromatography.

EXAMPLE 14

5'-deoxy-5'-propylthioadenosine

Analogously to Example 13, the product of Example 1 is reacted with propanethiol to produce the captioned product.

HYDROLYSIS OF THE NUCLEOSIDES

EXAMPLE 15

5-deoxy-5-ethylthioribose (ethylthioribose) (ETR)

The product of Example 13 is suspended in 4 ml of 0.1 m HCl at 100° C. After 2.5–3 hours, the reaction mixture is cooled and the pH is raised to 3.5. Separation of the desired product from adenine and any residual unhydrolyzed nucleoside is accomplished through cation exchange chromotography using DOWEX 50H+.

EXAMPLE 16

5-deoxy-5-propylthioribose

Analogously to Example 15, the product of Example 14 is hydrolyzed to produce the captioned product.

INHIBITION OF THE GROWTH OF MTR KINASE-DEPENDENT MICROORGANISMS

In the following examples, an MTR kinase-dependent microorganism is treated in vitro with compounds of this invention. In the following examples, LB is a growth medium (Luria-Bertani) containing, per liter, 10 grams Bacto-tryptone, 5 grams Bacto-yeast extract and 10 grams NaCl. $OD_{550}$ is a measure of the optical density of the suspension at the indicated time. Low optical density indicates a low cell concentration in the suspension and thus that compounds were effective to inhibit the growth of the microorganisms. An optical density of 0 indicates that no growth occurred.

EXAMPLE 17

Treatment of *Candida albicans* with 5-Deoxy-5-Ethylthioribose

| Tube # | Additions ETR Stock | [ ] | LB broth ML | 0.1 ml Cells | $OD_{550}$ at 24 Hrs | Growth at 7 days |
|---|---|---|---|---|---|---|
| 1 | 1 ml* | 9.2 mM* | 1.0 | $10^4$ | 0.0 | -- |
| 2 | 0.5 | 4.6 mM | 1.50 | $10^4$ | 0.0 | -- |
| 3 | 0.25 | 2.3 mM | 1.75 | $10^4$ | 0.0 | -- |
| 4 | 0.1 | 0.9 mM | 1.90 | $10^4$ | 0.120 | + |
| 5 | 0.05 | 0.46 mM | 1.95 | $10^4$ | 0.357 | ++ |
| 6 | 0.025* | 0.23 mM | 1.975 | $10^4$ | 0.355 | ++ |
| 7 | 0.010 | 0.092 mM | 1.99 | $10^4$ | 0.409 | ++ |
| 8 | Control | | 2.0 | $10^4$ | 0.413 | ++ |

*Total Vol. = 2.0 mls.

EXAMPLE 18

Treatment of *Candida albicans* with 5-Deoxy-5-Ethylthioribose (ETR)

(ETR* vs High Dose *Candida inoculum*)

| Tube # | LB broth | ETR | $H_2O$ | Blasto-candida | 24 hrs $OD_{550}$ | Growth at 72 Hrs |
|---|---|---|---|---|---|---|
| 1 | 1.5 mls | 0.5 ml | | $10^2$ | 0.000 | -- |
| 2 | 1.5 mls | 0.5 ml | | $10^3$ | 0 | -- |
| 3 | 1.5 mls | 0.5 ml | | $10^4$ | 0 | -- |
| 4 | 1.5 mls | 0.5 ml | | $10^5$ | 0 | -- |
| 5 | 1.5 mls | 0.5 ml | | $10^6$ | 0.006 | -- |
| 6 | 1.5 mls | 0.5 ml | | $10^7$ | 0.008 | -- |
| 7 | 1.5 mls | -- | 0.5 mls | $10^2$ | 0.488 | ++ |
| 8 | 1.5 mls | -- | 0.5 mls | $10^3$ | 0.496 | ++ |
| 9 | 1.5 mls | -- | 0.5 mls | $10^4$ | 0.574 | ++ |
| 10 | 1.5 mls | -- | 0.5 mls | $10^5$ | 0.606 | ++ |
| 11 | 1.5 mls | -- | 0.5 mls | $10^6$ | 0.658 | ++ |
| 12 | 1.5 mls | -- | 0.5 mls | $10^7$ | 0.716 | ++ |

*Using 18.4 mM stock solution of ETR.

Examples 17 and 18 indicate that 5-deoxy-5-ethyl-5-deoxy-5-ethylthioribose clearly inhibits the growth of *Candida albicans*.

EXAMPLE 19

In this example, samples containing a known number of microorganisms were colonized without ETR and in the presence of ETR. In the instances where growth occurred, one colony formed for each microorganism. The microorganisms colonized in the presence of ETR formed less than 1,000 colonies, indicating that ETR is cytocidal to *Candida albicans*, as opposed to cytostatic.

Procedure:

| Stock Candida | LB Broth | Additions ETR | Time | Amount plated | Colonies |
|---|---|---|---|---|---|
| 1. -- | 0.1 ml | -- | 0 hr | 0.1   1 | 0 |
| 2. (0.1 ml)$10^3$ orgs | 1.9 ml | -- | 0 hr | 50    1 | 26 |
| 3. (0.1 ml)$10^3$ orgs | 1.9 ml | -- | 0 hr | 100   1 | 57 |
| 4. (0.1 ml)$10^3$ orgs | 1.9 ml | -- | 3 hrs | 100  1* | 116 |
| 5. (0.1 ml)$10^3$ orgs | 1.9 ml | 0.5 ml | 3 hrs | 100  1* | 2 |
| 6. (0.1 ml)$10^3$ orgs | 1.9 ml | -- | 5 hrs | 100  1* | 327 |
| 7. (0.1 ml)$10^3$ orgs | 1.9 ml | 1.5 ml | 5 hrs | 100  1* | 0 |

*1:10 dilution

Interpretation of Results:

| Vessel | Colonies | Dilution Factor | Total # Organisms |
|---|---|---|---|
| 1. BLANK | 0 | 1 | 0 |
| 2. Control (no ETR) | 26 | $\frac{50\,l}{2000\,l}$ or 40 | 1040 |
| 3. Control (no ETR) | 57 | $\frac{100\,l}{2000\,l}$ or 20 | 1120 |
| 4. 3 hrs incubation | 116 | $\frac{100\,l}{2000\,l}$ *or 200 | 23200 |
| 5. 3 hrs (+ETR) 4 mM | 2 | $\frac{100\,l}{2000\,l}$ *or 200 | 400 |
| 6. 5 hrs (w/o ETR) | 327 | $\frac{100\,l}{2000\,l}$ *or 200 | 65400 |
| 7. 5 hrs (w/ETR) 4 mM | 0 | $\frac{100\,l}{2000\,l}$ *or 200 | 0 |

*1:10 dilution

EXAMPLE 20

Treatment of *Candida albicans* with 5-Chloro-5-Deoxyribose

| Tube # | 10 mM Stock 5-chloro | LB | Cells | $OD_{550}$ 24 hrs | $OD_{550}$ 7 days |
|---|---|---|---|---|---|
| 1 | -- | 2.0 ml | $10^4$ (.1 ml) | 0.431 | 1.739 |
| 2 | 0.2 | 1.8 | $10^4$ | 0.0 | 0.0 |
| 3 | 0.4 | 1.6 | $10^4$ | 0.0 | 0.0 |
| 4 | 0.8 | 1.2 | $10^4$ | 0.0 | 0.0 |

Example 20 demonstrates that 5-chlororibose is effective to kill *Candida albicans*.

TREATMENT OF BONE MARROW CELLS WITH ETHYLTHIORIBOSE

In the following examples, human bone marrow and mouse marrow cells were subjected to ethylthioribose. In each case, a preparation of immature blood cells from bone marrow were conventionally stimulated to mature in a gel matrix. Immature human granulocytic precursor (CFU-GM) cells formed a colony in the matrix and the number of cells in the colony was counted. Such tests are believed to be a good measure of the toxicity of the subject compounds to humans.

EXAMPLE 21

ETR: Toxicity toward Human Bone Marrow Function in vitro
CFU-GM assays as usual
30 cc at $8.9 \times 10^6$/cc, LD $10.4 \times 10^6$/cc (5 cc)
Total volume of each culture—1 ml.

| Marrow | ETR | P+ Serum (not applicable) | C' (not applicable) | CFU-GM ($2 \times 10^5$ total cells/plate) |
|---|---|---|---|---|
| 1 | + | -- | " | " | 54,57 |
| 2 | + | 100 ml (stock)* | | | 50,51 |
| 3 | + | 100 ml (1:1) | | | 51,52 |
| 4 | + | 100 ml (1:2) | | | 50,53 |
| 5 | + | 100 ml (1:4) | | | 54,55 |
| 6 | + | 100 ml (1:10) | | | 53,51 |
| 7 | + | 100 ml (1:20) | | | 55,52 |
| 8 | + | 100 ml (1:40) | | | 54,55 |
| 9 | + | 100 ml (1:50) | | | 52,56 |

-continued

| Mar-row | ETR | P+ Serum (not applicable) | C' (not applicable) | CFU-GM ($2 \times 10^5$ total cells/plate) |
|---|---|---|---|---|
| 10 | + | 100 ml (1:100) | | 53,53 |
| 11 | + | 100 ml (1:1000) | | 54,51 |
| 12 | + | 100 ml (1:10k) | | 51,50 |
| 13 | + | 100 ml (1:100k) | | 55,53 |

*Concentration of ETR Stock - 18.4 mM

EXAMPLE 22

ETR: Toxicity toward mouse marrow

| | ($0 \times 10^6$/ml) Marrow | ETR | CFU-GM |
|---|---|---|---|
| 1 | 10 | none | 37,40 |
| 2 | 10 | 100 (stock) | 35,36 |
| 3 | 10 | 100 (1:1) | 34 — |
| 4 | 10 | 100 (1:2) | 37,33 |
| 5 | 10 | 100 (1:4) | 32,34 |
| 6 | 10 | 100 (1:10) | 36,34 |
| 7 | 10 | 100 (1:40) | 33,35 |
| 8 | 10 | 100 (1:50) | 37,36 |
| 9 | 10 | 100 (1:100) | 39 — |
| 10 | 10 | 100 (1:1k) | 36,37 |
| 11 | 10 | 100 (1:10k) | 35,32 |
| 12 | 10 | 100 (1:100k) | 33,35 |
| 13 | 10 | 100 (1:20k) | 32,34 |

The following examples illustrate the effect of ETR on the growth of protozoans.

EXAMPLE 23

Toxicity of ETR to Ochromonas malhamensis (ATCC #11532)

a. Procedure.

2 ml cultures of *O. malhamensis* were set up at a cell density of $4 \times 10^4$ per ml. The culture medium used was thioglycolate broth and incubation took place at ambient temperature near a south-facing window (these organisms are photosynthetic). ETR was added at the appropriate dilution at the beginning of the experiment. Cell number was determined using a hemacytometer. The data (shown below) were obtained after 48 hours of incubation.

b. Results.

| Condition | Cell density (Day 2) |
|---|---|
| Control (no additions) | $1.28 \times 10^6$ per ml |
| $+10^{-5}$ M ETR | $1.25 \times 10^6$ per ml |
| $+2 \times 10^{-5}$ M ETR | $0.6 \times 10^6$ per ml |
| $+5 \times 10^{-5}$ M ETR | $0.03 \times 10^6$ per ml |
| $+10 \times 10^{-5}$ M ETR | $0.03 \times 10^6$ per ml |
| $+20 \times 10^{-5}$ M ETR | debris |

The results indicate that the $ID_{50}$ for ETR vs. *O. malhamensis* is 20 μM.

EXAMPLE 24

Inhibition of Giardia lamblia (Portland 1 strain) by ETR a. Procedure.

*Giardia lamblia* was cultured in Diamond's TP-S-1 medium supplemented with 10% heat-inactivated calf serum and antibiotics (penicillin and streptomycin). The antibiotics were added to prevent contamination by bacteria. Tube cultures containing 7 mls of medium were seeded with $5 \times 10^4$ organisms per ml and incubated horizontally at 37° C. for 48 hrs. ETR was added at the beginning of the experiment. Cell number was determined with the aid of a hemacytometer.

b. Results.

| | Total Cell Number ($\times 10^{-5}$) | | | |
|---|---|---|---|---|
| Condition | 5/23/86* | 11/7/86 | 11/22/86 | Average (SD) |
| Control | 7.65 | 6.0 | 8.2 | 7.28 (0.9) |
| +ETR (0.078 mM) | — | 6.0 | — | 6.0 |
| +ETR (0.156 mM) | 7.4 | 5.0 | 7.0 | 6.5 (1.0) |
| +ETR (0.312 mM) | 6.4 | 2.1 | 4.8 | 4.4 (1.7) |
| +ETR (0.625 mM) | 4.3 | 1.0 | 3.7 | 3.0 (1.4) |
| +ETR (1.24 mM) | 4.1 | 0.6 | 2.8 | 2.5 (1.4) |
| +ETR (2.50 mM) | 2.1 | debris | 1.5 | 1.8 (0.3) |
| +ETR (5.0 mM) | 0.3 | debris | 0.7 | 0.5 (0.2) |

*Cysteine added to the point of precipitation.

The results indicate that the $ID_{50}$ for ETR vs. *G. lamblia* appears to be near 0.45 mM. There is significant cell death and lack of "swimming" at concentrations ranging from 0.62 mM to 5 mM.

EXAMPLE 25

Effect of ETR on Plasmodium falciparum in vitro a. Procedure.

Parasitized erythrocytes from a stock four-day-old culture at approximately 10% infection were mixed with washed clean erythrocytes to give a final parasitemia of approximately 1%. Using 1.2 cm plastic Petri dishes duplicate 1 ml cultures were initiated with drug dilutions in complete RPMI-1640, containing 0.1 ml of erythrocytes and 50 ug of gentamycin/ml. The cultures were supplemented with RPMI-1640 (25 mM HEPES), 0.24% sodium bicarbonate and 10% human serum (Type A⁻). All cultures were gassed with 90% nitrogen, 5% carbon dioxide and 5% oxygen prior to incubation at 37° C. Parasite growth was assessed by microscopic evaluation of Giemsa-stained thin-smears.

b. Results.

| | Percent Parasitemia* | | | | |
|---|---|---|---|---|---|
| Conditions | 24 hrs | 48 hrs | 72 hrs | 96 hrs | 120 hrs |
| Control (no additions) | 3.8 | 7.1 | 10.8 | 18.0 | 30.0 |
| +5 mM ETR | 0.3 | 0.9 | 0.8 | 0.6 | 0.6 |
| +2 mM ETR | 0.5 | 0.6 | 0.8 | 0.7 | 0.5 |
| +1 mM ETR | 0.9 | 1.3 | 0.8 | 0.8 | 0.5 |

*The results reflect the average of counts from three independent investigators. The drug was removed after 48 hrs. and replaced by complete medium. That the parasitemia did not reappear after the drug was removed suggests that ETR is cidal.

Microscopic examination of Giemsa-stained smears showed that 5-ethylthioribose (ETR) was inhibitory to *P. falciparium*-infected cultures. The control culture produced a continuous and progressive infection. The anti-parasitic effect of ETR was apparent at the lowest concentration tested. After 24 hours in the presence of 1 mM ETR a small increase in growth was noted but the parasites appeared abnormal. By 48 hours the parasitemia had decreased to less than 0.1% (initial seeding was <1.0%) with a noticeable amount of debris in the stained smears. By 72 hours the infection was assessed to be less than 1 parasite per 10,000 red cells and only abnormal pyknotic forms remained. 1 mM and 5 mM produced an immediate and pronounced effect on the course of the culture infection. In both cultures after 24 hours the parasitemia had remained at or below the level of the initial inoculum and only abnormal "crisis" forms could be seen. By 72 hours, all drug-treated cultures were completely negative. It is of interest that after 5 days (the last 3 days without drug) the parasitemia did not reappear.

The results show that ETR is inhibitory toward *P. falciparum* in vitro. In addition, all observers noted that only abnormal pyknotic forms existed in drug-treated cultures beyond 48 hours. These forms are called "crisis" forms and are considered to be non-viable parasites.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula:

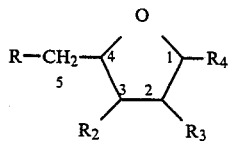

wherein R is $R_1S-$ in which $R_1$ is $C_1-C_{10}$ linear or branched chain alkyl or halogenated linear or branched chain alkyl, wherein $R_2$, $R_3$ and $R_4$ are the same or different and each is H or OH, with the proviso that at least one of $R_2$, $R_3$ and $R_4$ is hydroxy and the further proviso that when $R_2$, $R_3$ and $R_4$ are all OH, $R_1$ is other than methyl or isobutyl.

2. A compound of claim 1 wherein $R_2$, $R_3$ and $R_4$ each are OH.
3. A compound of claim 1 wherein $R_1$ is $CH_3CH_2-$.
4. 5-Ethylthioribose, a compound of claim 1.
5. A compound of claim 1 wherein $R_1$ is halogenated alkyl.
6. A compound of claim 1 wherein $R_1$ is alkyl.
7. A compound of claim 6 wherein $R_1$ is hexyl.
8. A compound of claim 6 wherein $R_1$ is heptyl.
9. A compound of claim 6 wherein $R_1$ is octyl.
10. A compound of claim 6 wherein $R_1$ is nonyl.
11. A compound of claim 6 wherein $R_1$ is decyl.
12. A pharmaceutical composition comprising an amount of a compound effective to inhibit the growth of an MTR kinase-dependent microorganism, in a suitable carrier, wherein the compound is of the formula

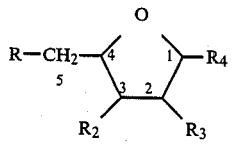

wherein R is $R_1S-$, in which $R_1$ is $C_1-C_{10}$ linear or branched chain alkyl or halogenated alkyl,
wherein $R_2$, $R_3$ and $R_4$ are the same or different and each is H— or —OH, with the proviso that at least one of $R_2$, $R_3$ and $R_4$ is —OH and the further proviso that when $R_2$, $R_3$ and $R_4$ are all —OH, $R_1$ is other than methyl.

13. A composition of claim 12, wherein the compound is 5-ethylthioribose.
14. A composition of claim 12, wherein $R_2$, $R_3$ and $R_4$ each are OH.
15. A method of treating a mammal infected with a 5-deoxy-5-methylthioribose (MTR) kinase-containing microorganism, comprising administering systemically, to said mammal an amount effective to ameliorate the infection, of a compound of the formula

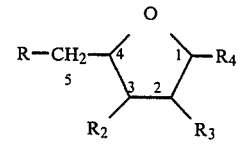

wherein R is H—, Cl—, F—, Br—, I— or $R_1S-$, in which $R_1$ is $C_1-C_{10}$ linear or branched chain alkyl or halogenated $C_1-C_{10}$ linear or branched chain alkyl, wherein $R_2$, $R_3$ and $R_4$ are the same or different and each is H— or —OH with the proviso that at least one of $R_2$, $R_3$ and $R_4$ is —OH and the further proviso that when $R_2$, $R_3$ and $R_4$ are all —OH, $R_1$ is other than methyl.

16. A method of claim 15 wherein $R_2$, $R_3$ and $R_4$ each are OH.
17. A method of claim 16 wherein R is $R_1S-$.
18. A method of claim 15 wherein the compound administered is 5-ethylthioribose.
19. A method of claim 15 wherein R is Cl.
20. A method according to claim 15 wherein the compound administered is 5-chlororibose.
21. A method of claim 15 wherein the infection is present on mammalian skin.
22. A method of claim 21 wherein the compound applied is 5-ethylthioribose and the amount thereof applied is a biocidally effective amount.
23. A method of claim 21 wherein the compound applied is 5-chlororibose and the amount thereof applied is a biocidally effective amount.
24. A method of claim 21 wherein the microorganism is a fungus.
25. A method of claim 24 wherein $R_2$, $R_3$ and $R_4$ each are OH.
26. A method of claim 24 wherein the fungus is *Candida albicans*.
27. A method of claim 26 wherein R is $R_1S-$.
28. A method of inhibiting the growth of an MTR kinase-containing microorganism comprising applying to the habitat thereof a metabolization-inhibiting amount of a compound of the formula

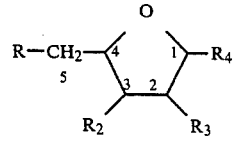

wherein R is H—, Cl—, F—, Br—, I— or $R_1S-$, in which $R_1$ is $C_1-C_{10}$ linear or branched chain alkyl or halogenated alkyl,
wherein $R_2$, $R_3$ and $R_4$ are the same or different and each is H— or —OH, with the proviso that at least one of $R_2$, $R_3$ and $R_4$ is —OH and the further proviso that when $R_2$, $R_3$ and $R_4$ are all —OH, $R_1$ is other than methyl.

29. A method of claim 28 wherein $R_1$ is halogenated alkyl.
30. A method of claim 28 wherein R is H.
31. A method of claim 28 wherein R is $R_1S$.
32. A method of claim 28 wherein $R_1$ is alkyl.
33. A method of claim 32 wherein $R_1$ is hexyl.
34. A method of claim 33 wherein $R_1$ is octyl.
35. A method of claim 34 wherein $R_1$ is decyl.
36. A method of claim 32 wherein $R_1$ is heptyl.
37. A method of claim 36 wherein $R_1$ is nonyl.
38. A method of treating a mammal infected with an MTR kinase-containing protozoan comprising administering thereto, an amount effective to ameliorate the infection, of a compound of the formula

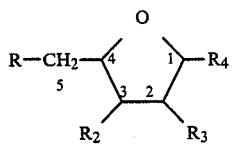

wherein R is H—, Cl—, F—, Br—, I— or $R_1S$—, in which $R_1$ is $C_1$-$C_{10}$ linear or branched chain alkyl or halogenated $C_1$-$C_{10}$ linear or branched chain alkyl, wherein $R_2$, $R_3$ and $R_4$ are the same or different and each is H— or —OH with the proviso that at least one of $R_2$, $R_3$ and $R_4$ is —OH and the further proviso that when $R_2$, $R_3$ and $R_4$ are all —OH, $R_1$ is other than methyl.

39. A method of claim 38 wherein the protozoan is parasitic.
40. A method of claim 39 wherein the protozoan is *Plasmodium falciparum*.
41. A method of claim 39 wherein the protozoan is *Giardia lamblia*.
42. A method of claim 39 wherein the protozoan is *Ochromonas malhamensis*.
43. A method of treating a mammal infected with an MTR kinase-containing microorganism, comprising administering, topically to said mammal, an amount effective to ameliorate the infection of a compound of the formula

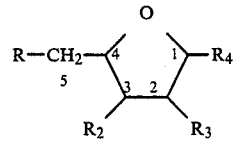

wherein R is H—, Cl—, F—, Br—, I— or $R_1S$—, in which $R_1$ is $C_1$-$C_{10}$ linear or branched chain alkyl or halogenated $C_1$-$C_{10}$ linear or branched chain alkyl, wherein $R_2$, $R_3$ and $R_4$ are the same or different and each is H— or —OH with the proviso that at least one of $R_2$, $R_3$ and $R_4$ is —OH and the further proviso that when $R_2$, $R_3$ and $R_4$ are all —OH, $R_1$ is other than methyl.

44. A compound of claim 43 wherein $R_2$, $R_3$ and $R_4$ each are OH.
45. A compound of claim 43 wherein $R_1$ is $CH_3CH_2$—.
46. A method of claim 43 wherein the compound is 5-ethylthioribose.
47. A method of claim 43 wherein $R_1$ is halogenated alkyl.
48. A method of claim 43 wherein $R_1$ is alkyl.
49. A method of claim 48 wherein $R_1$ is hexyl.
50. A method of claim 48 wherein $R_1$ is heptyl.
51. A method of claim 48 wherein $R_1$ is octyl.
52. A method of claim 48 wherein $R_1$ is nonyl.
53. A method of claim 48 wherein $R_1$ is decyl.

* * * * *